US009504509B2

(12) United States Patent
Reisberg

(10) Patent No.: US 9,504,509 B2
(45) Date of Patent: Nov. 29, 2016

(54) SYSTEM FOR OSTEOSYTHESIS OF THE STERNUM

(71) Applicant: MedXpert GmbH, Eschbach (DE)

(72) Inventor: Erhard Reisberg, Eschbach (DE)

(73) Assignee: MEDXPERT GMBH, Eschbach (DE)

( * ) Notice: Subject to any disclaimer, the term of this patent is extended or adjusted under 35 U.S.C. 154(b) by 186 days.

(21) Appl. No.: 14/160,813

(22) Filed: Jan. 22, 2014

(65) Prior Publication Data
US 2014/0207197 A1    Jul. 24, 2014

(30) Foreign Application Priority Data

Jan. 22, 2013 (DE) .................. 10 2013 000 972
Mar. 5, 2013 (DE) .................. 10 2013 102 178

(51) Int. Cl.
A61B 17/88   (2006.01)
A61B 17/82   (2006.01)
A61B 17/80   (2006.01)

(52) U.S. Cl.
CPC ......... *A61B 17/8872* (2013.01); *A61B 17/823* (2013.01); *A61B 17/8863* (2013.01); *A61B 17/8023* (2013.01); *A61B 17/8076* (2013.01); *A61B 17/8085* (2013.01); *A61B 2090/061* (2016.02)

(58) Field of Classification Search
CPC .. A61B 17/82; A61B 17/88; A61B 17/8872; A61B 17/823
USPC .............. 606/280–331, 86 R, 102, 101, 905
See application file for complete search history.

(56) References Cited

U.S. PATENT DOCUMENTS

| 4,201,215 | A | 5/1980 | Crossett et al. | |
|---|---|---|---|---|
| 6,293,949 | B1 * | 9/2001 | Justis | A61B 17/7011 606/279 |
| 6,872,210 | B2 * | 3/2005 | Hearn | A61B 17/8009 606/281 |
| 7,473,257 | B2 * | 1/2009 | Knopfle | A61B 17/8863 606/101 |
| 2002/0111643 | A1 | 8/2002 | Herrmann et al. | |
| 2004/0176780 | A1 | 9/2004 | Knopfle | |
| 2005/0267475 | A1 * | 12/2005 | Miller, III | A61B 17/823 606/324 |
| 2008/0082101 | A1 | 4/2008 | Reisberg | |

(Continued)

FOREIGN PATENT DOCUMENTS

| CN | 202235649 U | 5/2012 |
|---|---|---|
| DE | 295 14 830 U1 | 2/1996 |

(Continued)

OTHER PUBLICATIONS

European Search Report, dated Mar. 24, 2014, from corresponding EP application.

(Continued)

*Primary Examiner* — Christopher Beccia
(74) *Attorney, Agent, or Firm* — Young & Thompson

(57) ABSTRACT

An implant 1 for sternal osteosynthesis has a clamp 10 with a first prong 101, a second prong 102 and a connecting portion 100. In the connecting portion 100 is formed a member 11 for the purpose of providing engagement with or for positionally stable support for a compatible supporting member of a bending tool (not shown). On both sides of the connecting portion 100 of the clamp 10, the member 11 has protrusions, which, together with the edges of the connecting portion, form angles for the purpose of engagement of the bending tool.

16 Claims, 8 Drawing Sheets

(56) References Cited

U.S. PATENT DOCUMENTS

2011/0060372 A1 3/2011 Allison
2011/0106182 A1 5/2011 Reisberg
2014/0207197 A1 7/2014 Reisberg

FOREIGN PATENT DOCUMENTS

| DE | 199 35 418 A1 | 2/2001 |
| DE | 103 01 692 A1 | 8/2004 |
| DE | 10 2006 042 277 A1 | 3/2008 |
| DE | 10 2008 002 389 A1 | 1/2010 |
| DE | 10 2013 102 178 | 7/2014 |
| GB | 2471855 A | 1/2011 |
| WO | 2010004602 A1 | 1/2010 |

OTHER PUBLICATIONS

International Search Report, dated May 6, 2014, from corresponding PCT application.
DE Office Action, dated Jan. 19, 2016; Application No. 10 2013 102 178.6.
DE Office Action, dated Jan. 19, 2016; Application No. 10 2013 022 286.9.
DE Office Action, dated Jan. 19, 2016; Application No. 10 2013 022 285.0.
DE Office Action, dated Jan. 19, 2016; Application No. 10 2013 022 279.6.

* cited by examiner

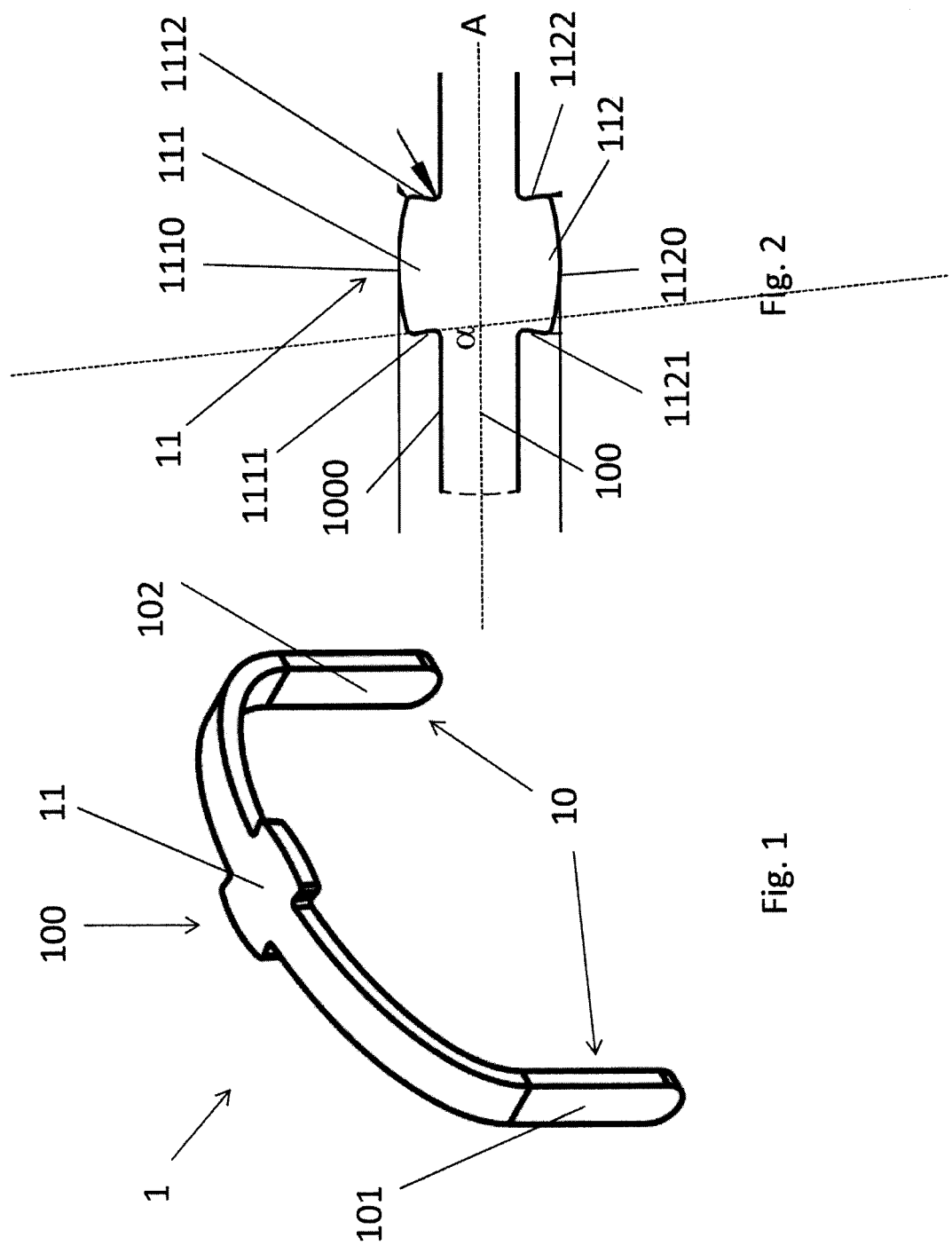

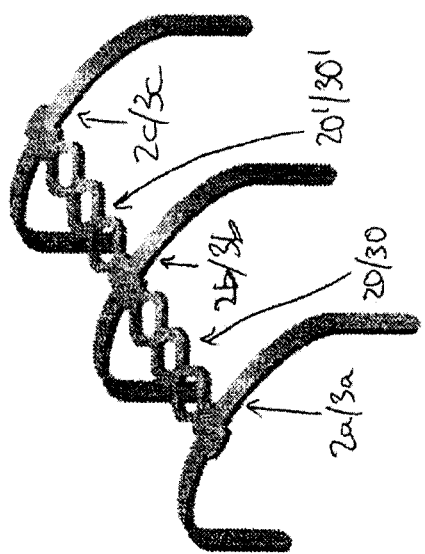
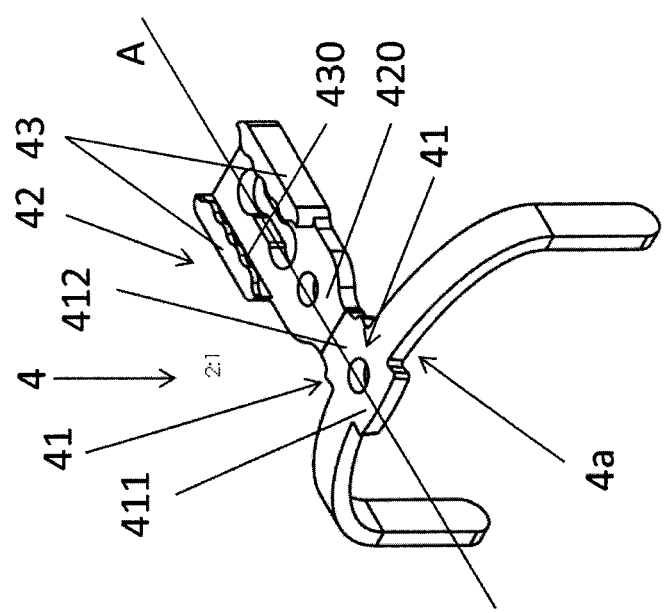
Fig. 5
Fig. 6

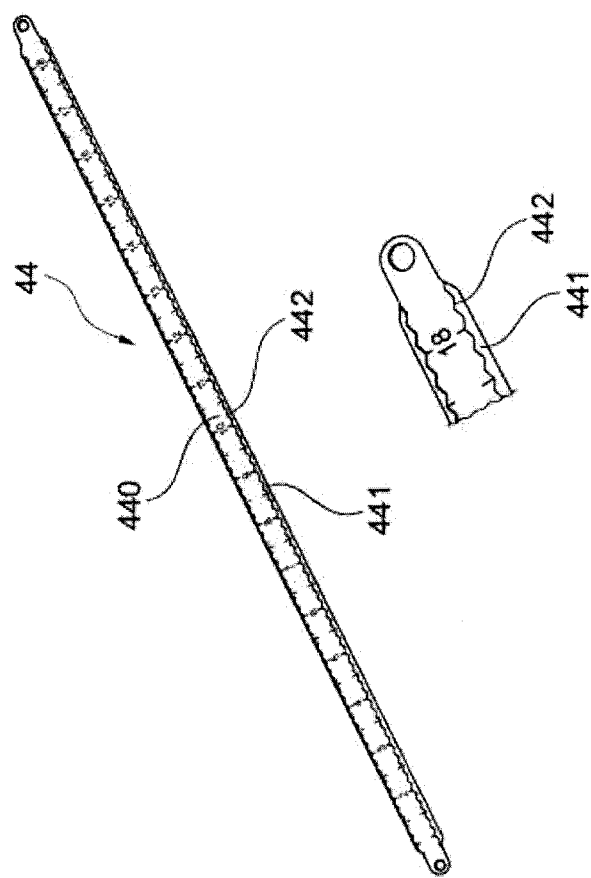

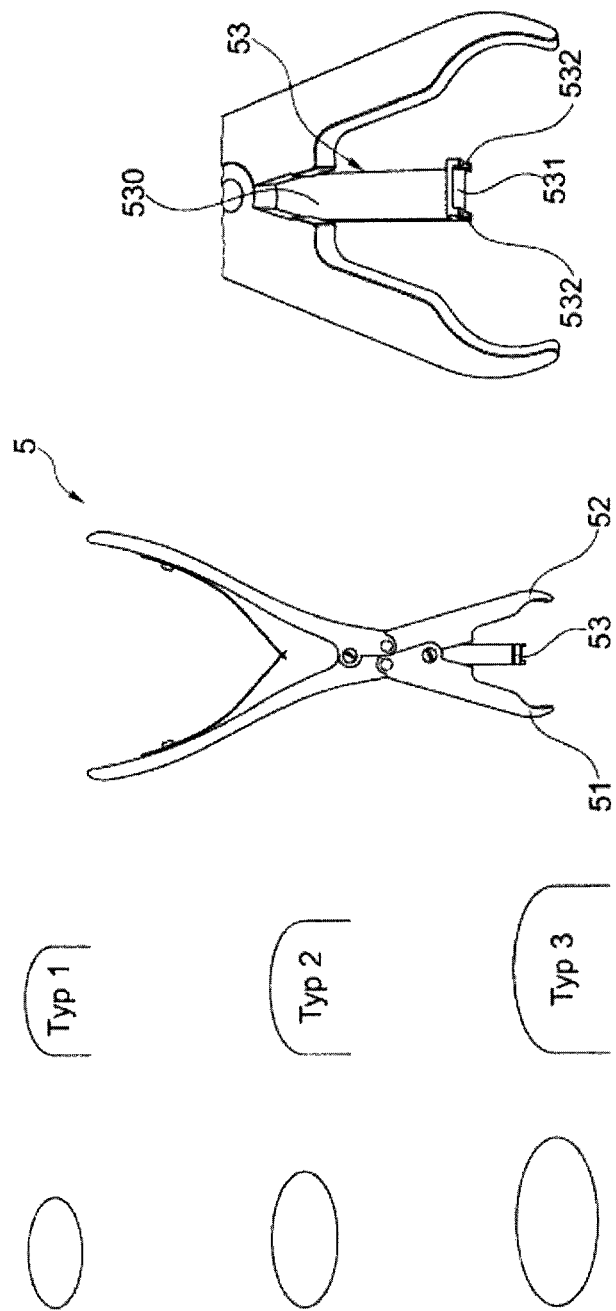

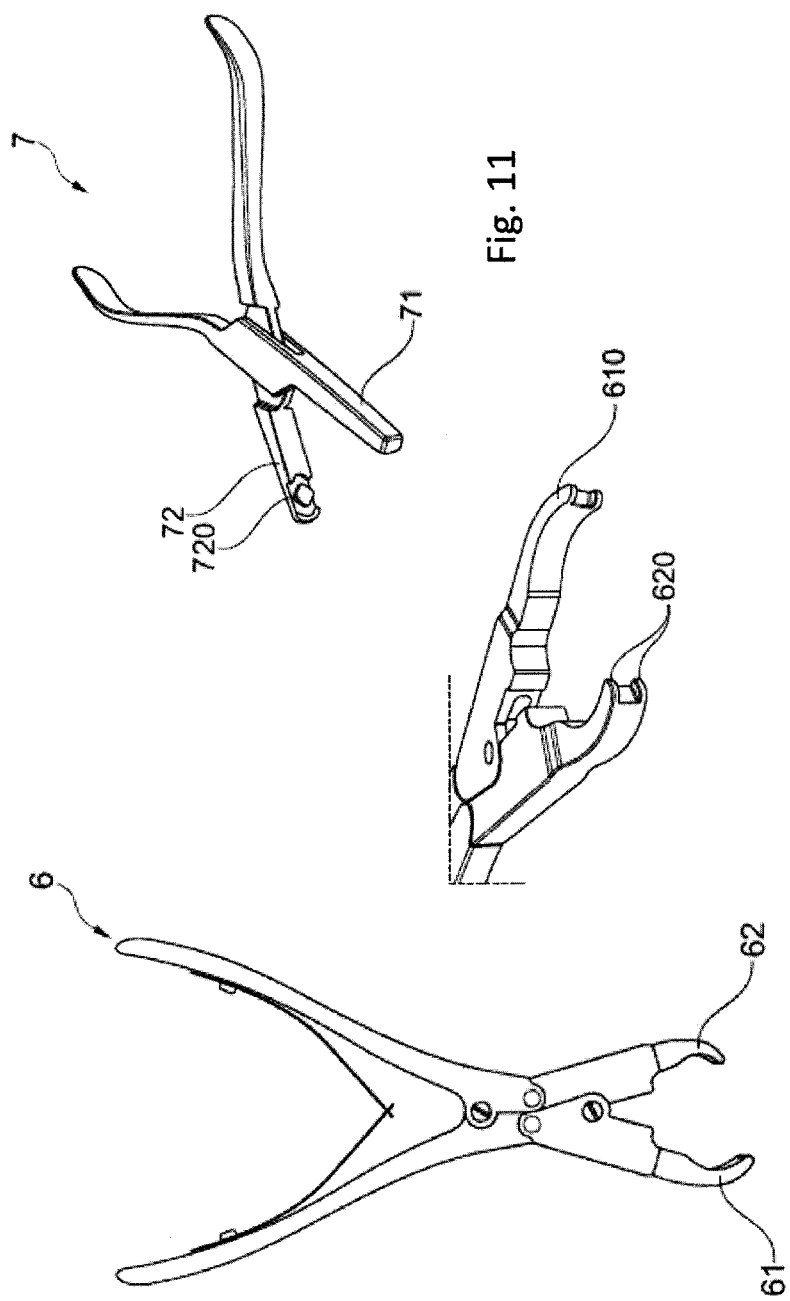

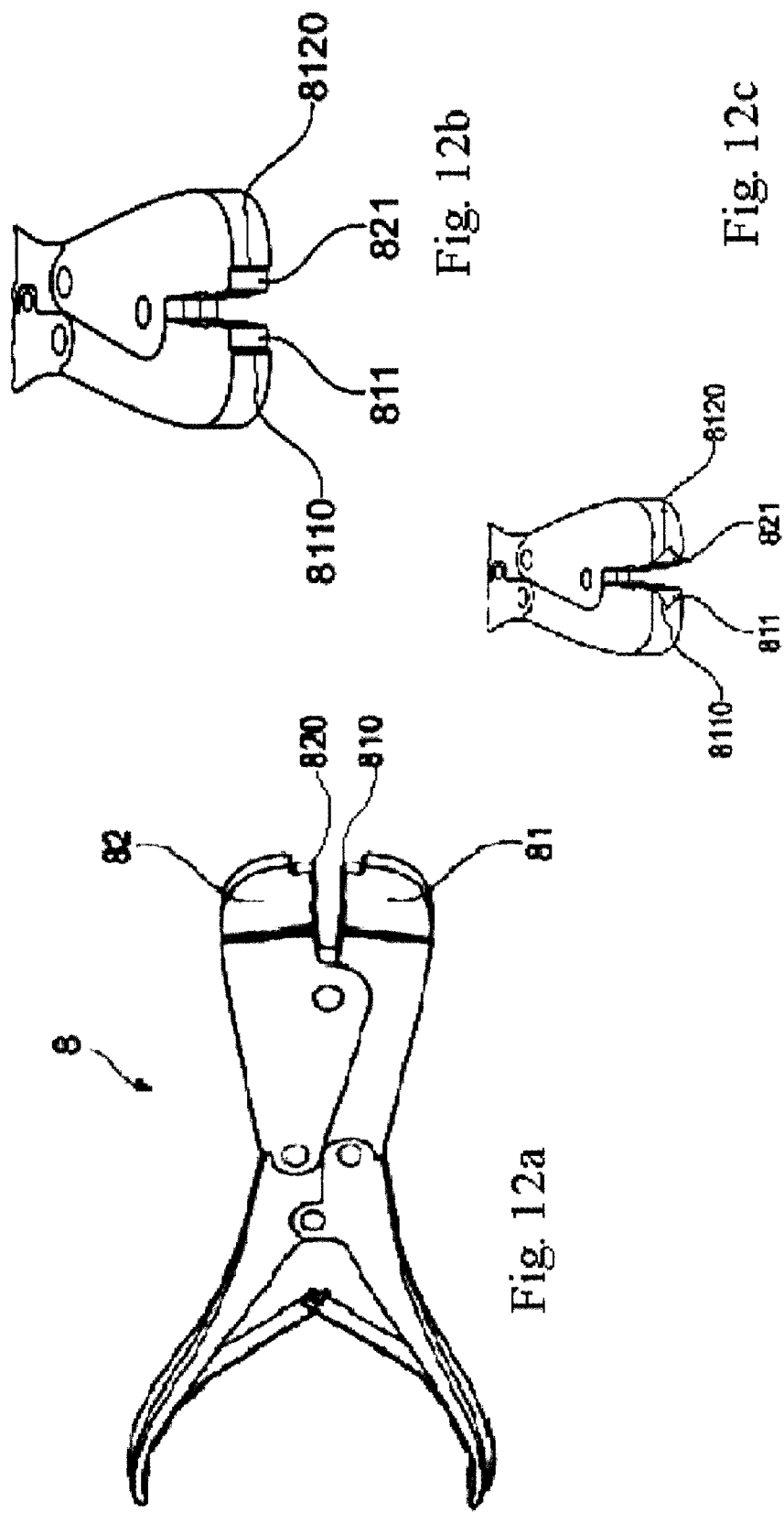

SYSTEM FOR OSTEOSYTHESIS OF THE STERNUM

TECHNICAL FIELD

The present application relates to an implant component for sternal osteosynthesis, comprising a clamp having a first prong and a second prong, with the first prong and the second prong connected by a connecting portion. The invention also relates to implants for sternal osteosynthesis, an implant system for sternal osteosynthesis and a series of implant-selection and manipulating instruments, as well as bending, deforming and forming instruments for manipulating the implant components and implants.

PRIOR ART

The term "sternotomy" stands for the opening of the chest (thorax) in the area of the breastbone (sternum) to create access, for example, for open-heart surgery.

Partial or total sternotomy is used as an access route for operations on the organs of the mediastinum. Examples are open-heart surgery, insertion of aortocoronary bypasses, heart transplants, tumors of the thymus gland (very rare). In exceptional cases, partial sternotomy is also required for operations on very large retrosternal goiters (strumectomy, thyroidectomy).

A longitudinal incision is made along the breastbone. The skin and subcutaneous tissue are severed. Local hemostasis is obtained by means of electrocautery as far as the periosteal surface of the sternum. From top (suprasternal notch) and from below (xiphoid process), a blunt dissection is performed by running a finger under the sternum to separate the loose connective tissue at the back. With an oscillating saw or a special jig saw, the sternum is separated along the midline. The chest can then be opened to almost any width by means of a spreading device.

After completion of the procedure on the soft tissues in the chest, the sternum must be closed again, for which purpose wires made of implant steel are primarily used. Generally, closure of the sternum is effected by means of strong loops of wire passed through the intercostal spaces ("wire cerclage").

Wires are available in different material thicknesses and the "wiring" technique itself offers various options (sutures, figure-8 ligatures, etc).

A number of factors can lead to serious complications when wires are used. Already at the intraoperative stage, barely recognizable injury of blood vessels can be caused by the guide needle at the wire that need to be treated in revision surgery. If, for example, the wire suture fails at an early stage after the procedure and before the biological process of osteosynthesis (healing of the separated bone) of the sternum has progressed far enough, the two sternal halves "drift" apart again or rub together. This often has serious consequences for the patient:

The patient must undergo a second surgical procedure to provide secondary stabilization of the sternum. Apart from the operational risk arising from the second procedure itself, the risk of inflammation or infection necessarily increases, and the hospital stay and the overall healing period is extended considerably.

The consequences of postoperative deep sternal infection are often fatal. The patient mortality rate is 15-50%, due not only to the infection itself, but also to ruptures of the right ventricle.

The use of wire also has the following disadvantages:

To an extent depending on the material used or its diameter, the maximum tensile strength of the wire before material failure occurs is about 20-22 kg. As against that, it is known from the literature that a spontaneous coughing fit produces a pressure of about 150 kg in the chest cavity. Accordingly, at least six, preferably up to eight, wire ligatures are required for stabilizing a sternotomy in order that this pressure may be resisted. Even before material failure occurs, the wire "stretches" along its length if overloaded—seams can "come apart" or an extended gap open between the sternal halves that does not knit back together, the result of which is often instability of the anterior chest that can lead postoperatively to impaired wound healing, inflammation or wound infection.

During sternal closure, the two loose wire ends are held with a needle holder or similar surgical instrument and twisted around each other. Frequently, the held wire ends are rotated more than 4-5 times, as a result of which the wire itself becomes weakened or overstretched—a "predetermined breaking point" is created, which leads to material failure and undoing of the fixation within a few hours, days or weeks.

In patients suffering from restricted bone quality (e.g., osteoporosis), the small contact area of the wire on the bone leads to pressure necrosis, and the underlying bone dies. The wire "cuts into" or fractures the bone, a fact which can lead to a "loosening" of the fixation of the sternal halves with the consequences described above.

Surgical wire is usually made of implant steel (alloy of chromium-nickel-molybdenum), which can lead to massive foreign-body reactions in people with allergies. Thus, even where stabilization of the sternum is unimpaired, a reaction, triggered by the foreign material, can give rise to inflammation or infection or similar response of the tissue.

OBJECT OF THE INVENTION

The object of the present invention is to provide an implant for sternal osteosynthesis that ensures long-term, reliable stabilization of the osteotomized sternum. In addition, the implants are to be manipulable by suitable tools.

TECHNICAL SOLUTION

This object is achieved by the provision of an implant component, implants, an implant system, bending tools, and a measuring tool. Advantageous embodiments will become apparent from the characteristics of the dependent claims.

The inventive implant component, which can itself be a complete implant or a component of an implant having further elements, comprises a clamp having a first prong and a second prong, with the first prong and the second prong connected by a connecting portion. At the connecting portion is arranged a member for the purpose of providing engagement with a compatible positioning member of a bending tool or providing positionally stable support for a compatible positioning member of a bending tool. The member itself can be referred to as a positioning member, too, which cooperates with the compatible positioning member of the bending tool in order that said tool may be arranged so as to be positionally stable relative to the implant or the implant component. The positionally stable arrangement means that the positioning member of the bending tool is fixed as regards movement in one or two dimensions, that is to say, is immovable, with respect to the positioning member of the implant or the implant component. This is effected by positive-locking engagement which limits the directions of movement and the relative alignment of the positioning members.

Thus, the implant component has a member that can mutually cooperate with a compatible positioning member of a bending tool and/or can be brought into engagement therewith and/or can be securely or firmly fixed in position thereat. For example, a bending pliers can be provided with a hold-down device or a stationary (i.e., fixed in position at the implant, relative to the clamping jaws, during actuation of the pliers) fixing member which engages with the member for the purpose of mutual engagement and so is safely secured against changes of position along the surface of the sternum. The stationary fixing member is thus fixed in positive engagement in at least two dimensions, but can be released again from engagement again by lifting (the third dimension).

The member can however also be used to provide positionally stable support for a compatible positioning member of a bending tool. Thus, a first clamping jaw of a two jaw pliers can be supported at the member while the other clamping jaw is being actuated. Said first jaw is stationary during the bending operation, that is to say, it is supported in a fixed position with respect to the implant. Positionally stable supporting means that the first clamping jaw of the pliers can be placed at the member such that the member is fixed at least relative to movements transverse to the direction of movement of the movable tool part. Removal from the abutting engagement is possible only counter to the direction of movement of the movable tool part. The compatible positioning member can to a certain extent be hooked to the member for the purpose of providing engagement and support.

The implant component can serve for secondary procedures as well as being the standard for primary stabilization of the sternum after sternotomy. It has three-dimensional functional stability, can be used variably, only a few variants thereof are needed, and the design of the implant component requires few implant variants, etc. In particular, simple, time-saving handling is guaranteed.

Preferably, the implant component (as well as the implants described in the following) are made of biocompatible material. This can avoid the need for a second surgical procedure for the purpose of removing material. One candidate material is, e.g., titanium. Titanium can remain indefinitely in the body. Given that, due to the material and to the modified geometry of the clamp to suit the anatomy, neither biological nor cosmetic reasons (palpability of the clamp) indicate subsequent metal removal, a second procedure can be omitted.

Application at a sternum is carried out as follows:

First, a clamp of suitable size is selected and guided over the sternum, with the prongs of the clamp face down initially. Then a first bending tool, an implant-deforming pliers, is used to bend the prongs inward under the sternum through about 45°. Finally, with the aid of a further tool, an implant forming pliers is used to bend the ends of the prongs to make contact with the underside of the sternum.

The method utilizes the fact that the clamp does not need to be fully passed under the sternum, but rather only slight engagement behind the sternum is sufficient to securely fix the implant component or to ensure the necessary stability. As a result, the invasiveness of the procedure is substantially reduced, if not totally minimized. The risk of injury to tissue or vessels is minimized.

The implant component is formed essentially as a clamp. The clamp does not completely enclose the sternum (but more than 50% of it) and can be used in all the intercostal spaces (spaces between the ribs) along the entire length of the sternum.

If a complication or a later emergency arises that requires rapid reopening of the sternum, each implant component can, within a short period of time and by means of standard instruments (raspatory, periosteal elevator, pincers, etc.) available in every hospital, be lifted or separated and the sternum reopened. Of advantage is the fact that the implant component can, where necessary, also be removed quickly in hospitals that do not have implant-specific removal tools.

The inventive member for the purpose of providing engagement with or support for a compatible positioning member of a bending tool makes it possible to manipulate the implant component or the implant with tools that must be positioned exactly and perhaps have to hold the clamp in position.

The member for the purpose of providing engagement or support preferably comprises a first protrusion, which extends laterally from a first side of the connecting portion, and a second protrusion, which extends laterally from the opposite side of the connecting portion. The member for the purpose of providing engagement or support may not significantly complicate the structure of the implant component and any design-related geometries may not be present that impede the patient or the surgeon. As a result of the forming of lateral protrusions having the same strength/thickness as the neighboring connecting portion, no elevations are present that might be palpable even after the operation. The structure is simple, and offers at the same time an efficient way to reliably manipulate the implant component during the operation.

It is preferred that the protrusions are arranged at both sides of the connecting portion symmetrically. They may have the shape of a butterfly. I.e. the dimensions of the protrusions can be such that the protrusions are broader outwardly (away from the connecting portion) than near the connecting portion. Thus undercuts are formed behind the end edges, i.e. the side edges have recessed portions.

The protrusions create in particular four "hook-in points" that serve as an insertion point for a hold-down device of a preforming pliers. The stationary hold-down device which engages with the member for the purpose of providing engagement or support is provided because a clamp whose prongs are pressed together with pliers, lifts up. This allows the prongs to be bent inward by about 45°.

Thereafter, precision molding is performed by means of pliers having jaw parts/clamping jaws of two different lengths. The member for providing engagement or support serves here as anchoring points for the short jaw part of a compatible rib-clamp fixing-pliers. In order that the guide lugs at the jaw end can hook in well, the angle between the protrusion and the connecting portion is acute, i.e. less than 90°. The guide lugs can thus be securely positioned at the implant.

Small radii are required at the transition of the protrusion to the axial portion, and also at the long base of the rhombus above and below.

Specifically, the first protrusion and/or the second protrusion have a first end edge and/or a second end edge and two side edges, with the side edges of the protrusion and/or of the protrusions forming an angle with the respective side edge of the connecting portion for the purpose of providing engagement with the positioning member of the bending tool and for the purpose of making contact with the respective edges.

The side edges can form an acute angle with the respective edge of the connecting portion. The shape of each of the protrusions is thereby roughly trapezoidal, with the end edges longer than the connecting line between the connecting portion and the respective protrusion. As a result, the non-parallel sides (side edges) of the trapezoid extend outward at an acute angle, relative to the edge of the connecting fillet. The side edges can be slightly curved and in any case form an angle of less than 90° with the edges of the connecting portion, such that the bending tool can be securely positioned.

In particular, the angle can be greater than 60°, in particular greater than 80°, and smaller than 90°, in particular smaller than 85°. The angle will often lie between about 80° and 85°.

The first end edge and/or the second end edge can be curved. In particular, they are curved outward so as to be convex.

The surface of the member for providing engagement or support is in particular flush with the connecting portion of the clamp. This is made possible by the design of the formation of lateral protrusions as a member for the purpose of providing engagement and/or support. Thus, it is not necessary to form any elevations or protrusions at the top of the implant component that can hinder the surgeon and the patient. The implant thus remains largely unnoticed, and a secondary operation for the purpose of removal can thus be dispensed with as a rule.

The first protrusion and/or the second protrusion preferably have the same thickness as the connecting portion of the implant.

The object is also achieved by an implant for sternal osteosynthesis, comprising: a first implant component as described above and a second implant component as described above, a connecting fillet that connects the first implant component and the second implant component. The connecting fillet has at least one, preferably a plurality of fillet members, arranged adjacently along an axis, with the fillet member(s) each having a frame that defines an opening. Particularly, the length of the connecting fillet is adaptable according to the following description.

The connecting or central fillet of the implant should, in particular, be variable in length. The central fillet is intended to ensure that a divided sternum cannot be displaced in the longitudinal axis and is intended for oblique fractures of the sternum, e.g. as a result of car accidents, in which, e.g., the seat belt caused said oblique fractures. The central fillet should also be deformable in three-dimensions, if necessary torqueable and/or bendable up and down across its surface. This is realized by the structure of the connecting fillet of the present invention.

The frame and/or frames of the fillet members delimit(s) a roughly rectangular or rhombic opening, with the frame and/or frames so arranged that a diagonal of the rectangular/rhombic opening along the central axis, which extends perpendicularly to the clamps along the connecting fillet, lies on the axis. As a result, deformability in the form of elongation and shortening of the fillet are supported.

Preferably, the connecting fillet has two outer fillet members and one or more internal fillet members arranged adjacently in series, with the two outer fillet members each arranged at one end edge of the protrusion of the first implant component and/or of the second implant component.

The connecting fillet has, in particular, the same thickness as the clamp and/or the member for the purpose of providing engagement with or support for a compatible positioning member of a bending tool.

The clamp of the first implant component can have a different span than the clamp of the second implant component.

This implant can in principle be produced as a double-T clamp and then bent. Variants having the same (symmetric T-shape) and different (asymmetric T-shape) clamp proportions can now be provided between the first and second implant components. The variants can be color coded.

A further inventive implant comprises: at least one implant component as described above, and an attaching device for attaching a rod-shaped connecting member at the attaching device, with the attaching device attached to the member for the purpose of providing engagement or support.

In this model, too, a reliable "hook-in point" for the fixing-pliers must be provided. This is ensured by including the inventive implant component in the structure of the implant.

The attaching device can have a base with a contact surface and guide members arranged laterally thereto, wherein the guide members each have a fillet and a guide protrusion that extends inwardly from the fillet's upper edge to form guide receptacles with one side portion of the contact surface, said receptacles having a U-shaped cross-section.

The guide protrusions of the guide members preferably have an engagement structure, particularly a toothed structure.

An inventive implant system comprises: at least one implant as described above, and a rod-shaped connecting member for insertion into the guide of the attaching device and for the purpose of attaching at the guide. For example, two implants with one guide each can be provided.

The rod-shaped connecting member has in particular an attaching portion with an engagement structure, in particular a toothed structure, which, for the purpose of attaching the rod-shaped connecting member to the guide, can be brought into engagement with the toothed structure of the guide fillets.

In all embodiments (which have two or more clamps) the number of clamps may be varied. Furthermore, one or more of the clamps may only have one prong at one side of the connecting fillet. The prongs may be arranged along the connecting fillet displaced relative to each other (staggered), and/or have different width.

An inventive bending tool comprises two clamping jaws and a positioning member for the purpose of providing engagement with and/or support for the bending tool at an implant component as described above and/or at an implant component of an implant as described above.

The positioning member can have at least two protrusions, e.g., two or four protrusions, for the purpose of supporting the bending tool at the member for the purpose of providing engagement with or support for the bending tool.

The positioning member can, for example, be formed as a hold-down device for the purpose of pressing the implant against the sternum during the clamping process performed by the two clamping jaws. A pair of pliers for the purpose of preforming is symmetrical and has a hold-down device.

In the case of an asymmetric pliers with positioning member, it must be taken into account that there is not very much space between the ribs next to the sternum to insert the gripping jaw part. Consequently, the pliers must not be too bulky. The object is to be able to guide the longer jaw part as closely as possible over the clamp downward around the sternum while the shorter jaw part is held in position at the implant via the positioning member. This is achieved by means of suitable geometry. With the help of the implant and the tool, the risk of injury to vessels and tissue to the side of the sternum is reduced.

A further bending tool is designed to bend a connecting piece of an implant as described above. The bending tool has two clamping jaws, with at least one clamping jaw having a protrusion for the purpose of providing engagement with an opening formed in the connecting fillet of the implant.

A further bending tool comprises two clamping jaws with edges which can be brought into contact with each other by actuating the bending tool, wherein, at the front side of the jaws is formed in each case a recess that extends outwardly from the respective edge, wherein the outer wall of the recess is curved such that a frame of a fillet member of an implant as described above can be gripped and, upon actuation of the bending tool, deformed.

Within the scope of the invention all combinations of implant components/implants and suitable (bending) tools are claimed.

An inventive instrument for determining the size of an implant to be inserted comprises two levers that can be rotated toward each other, a measuring device with a pointer arranged at the first lever and a scale arranged at the second lever, wherein the pointer displays a particular value on the scale as a function of the angle of rotation between the levers.

The scale can have an elongate section, formed for example as a metal strip, said section having juxtaposed fields that correspond to different ranges of angles of rotation between the levers. The fields can be color-coded to match the implant sizes. The elongate section can be bent in a certain radius, which corresponds in particular to the distance between the elongate member and the rotary axis connecting the levers.

With the aid of the instrument, it is possible to dispense with templates for determining the requisite implant sizes. Moreover, implants are delivered sterile to the surgeon, such that it is not possible to determine the correct size in terms of accuracy of fit intraoperatively by positioning and trying out different implants. The measuring instrument prevents a situation in which accurate-fit implants are determined intraoperatively only after several attempts.

The scale on the measuring instrument is color-coded. Thus, a metric reading does not have to be determined that must then be transferred to the scale, but rather, a purpose-built implant can be defined via the same color on the scale, without the need for "conversion". This is much more reliable and more direct than a "measurement" involving subsequent matching, via, e.g., metric tables. The display of a specific color on the scale immediately indicates the color of the implant to be used.

DESCRIPTION OF THE FIGURES

Further characteristics and advantages of the invention result from the following description of preferred embodiments using the figures. These show in FIG. 1 A first embodiment of an inventive implant;
FIG. 2 A section from FIG. 1;
FIG. 5 A fourth embodiment of the inventive implant;
FIG. 6 A fifth embodiment of the inventive implant;
FIG. 7 A connecting rod, which is used in a system with the implant from FIG. 5;
FIG. 8 A schematic representation of different types of implants of an implant system;
FIG. 9a A first bending tool to be used in inventive implant systems;
FIG. 9b A section from FIG. 8a;
FIG. 10a A second bending tool to be used in inventive implant systems;
FIG. 10b A section from FIG. 9a;
FIG. 11 A third bending tool to be used in inventive implant systems;
FIG. 12a A fourth bending tool to be used in inventive implant systems;
FIG. 12b A section from FIG. 12a;
FIG. 12c A further embodiment of FIG. 12a, and
FIG. 13 An inventive implant-selection device.

DETAILED DESCRIPTION OF PREFERRED EMBODIMENTS

Figure 4:
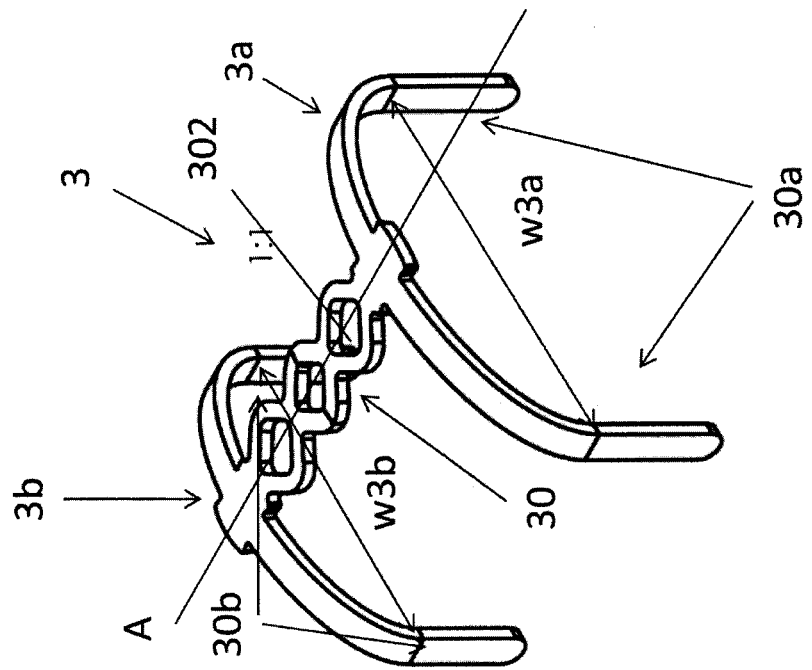
FIG. 4 A third embodiment of the inventive implant.

FIG. 1 shows a first embodiment of an inventive implant 1 and/or an inventive implant component 1 for sternal osteosynthesis. The implant 1 has a clamp 10 with a first prong 101, a second prong 102 and a connecting portion 100.

In the connecting portion 100 is formed, as per the invention, a member 11 for the purpose of providing engagement with or positionally stable support for a compatible supporting member of a bending tool (not shown). Preferably, the implant 1 is formed integrally and/or in one piece, for example, from titanium or other biologically neutral and/or bio-inert materials.

The member 11, which is shown in plan view in FIG. 2, has protrusions 111 and 112 on both sides of the connecting portion 100 of the clamp 10. The first protrusion 111 extends laterally on one side while the second protrusion 112 extends laterally on the other side. The protrusions 111 and 112 extend essentially perpendicularly to the outside from the connecting portion 100. The end edges 1110 and/or 1120 are essentially parallel with the edge 1000 of the connecting portion 100, but both are formed such that they curve slightly outward in a large radius. The essentially perpendicularly outwardly extending side edges 1111, 1112 and/or 1121, 1122 of the protrusions 111 and 112 each have an undercut, that is to say, the protrusions 111 and 112 widen toward their end edges 1110 and/or 1120. The angle α between the longitudinal axis A of the connecting portion 100 and the side edges 1111, 1112 and/or 1121, 1122 is slightly less than 90°, in particular between 60°, 70° and/or 80° and 85°. An engagement or support member of a bending tool can be securely positioned in the undercuts. Thus, on both sides of the connecting portion 100 of the clamp 10, the member 11 has protrusions which, together with the edges of the connecting portion, form an angle for the purpose of engagement with the positioning member of a bending tool.

Overall, the member 11 for the purpose of providing engagement with and/or support for a tool has a kind of butterfly shape, as the edges 1111 and 1121 and/or 1112 and 1122 each run at an obtuse angle of 2α to each other and the edges 1111 and 1112 and/or 1121 and 1122 are each formed as mirror images and symmetrically arranged.

Figure 3:
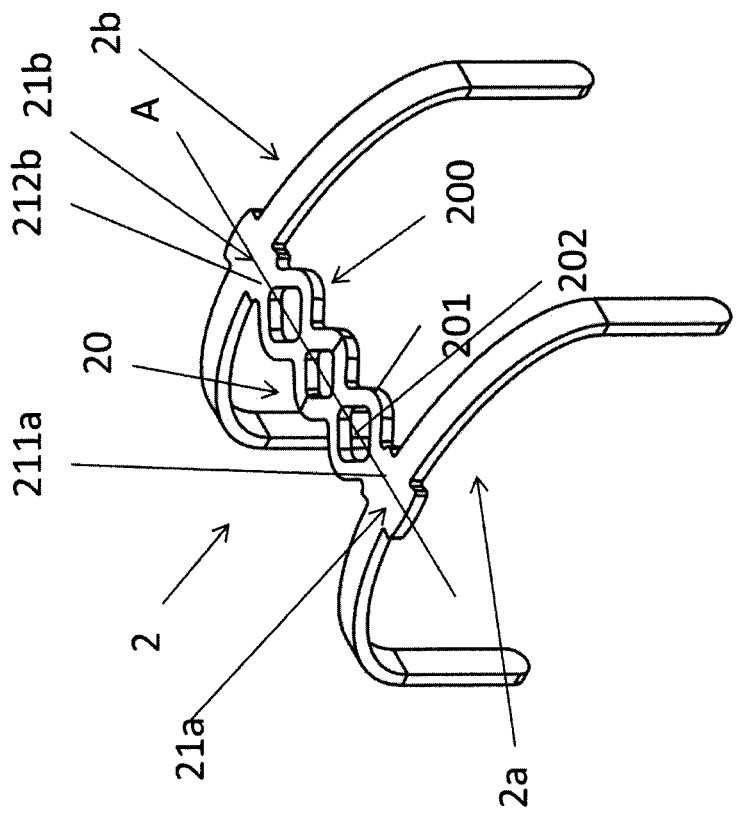
FIG. 3 A second embodiment of the inventive implant.

FIG. 3 shows a second embodiment of an inventive implant 2. The implant 2 has a first implant component 2a and a second implant component 2b that are connected via a connecting fillet 20. The implant components 2a and 2b each have essentially the same structure as the implant described in connection with FIGS. 1 and 2 and/or the implant component 1 as per the first embodiment. Corresponding elements are designated with the numeral "2" instead of "1" and a letter. For this reason, the structure of the first implant component 2a and the second implant component 2b will not be described in further detail.

The first implant component 2a and the second implant component 2b are connected via the connecting fillet 20 that extends between one of the protrusions 211a of the member 21a for the purpose of providing engagement with and/or support for a compatible supporting or positioning member of a bending tool of the first implant component 2a and one of the protrusions 212b of the member 21b for the purpose of providing engagement with and/or support for a bending tool of the second implant component 2b.

The connecting fillet 20 has fillet members 200—in the present case three fillet members 200—which are arranged adjacently along a longitudinal axis A of the connecting fillet 20. Each of the fillet members 200 has a frame 201 which defines a central opening 202. The opening is roughly quadratic with rounded corners. The fillet members 200 are each arranged such that one diagonal in each case extends along the longitudinal axis A. A first corner of the fillet members 200 is therefore connected to a protrusion 211a, 212b or to a corner of an adjacent fillet member 200. A second corner of the fillet members 200 that is opposite the first corner is connected to a corner of an adjacent fillet member 200. That is, one corner of the outer of the fillet members 200 is connected in each case to a protrusion 211a, 212b, while the other is connected to the corner of the adjacent fillet member 200. Opposite corners of the central or inner fillet members 200 are each connected to the corner of an adjacent fillet member 200.

The openings 202 of the fillet members 200 are intended and formed for engagement with a compatible engaging protrusion of a bending tool (FIG. 11, 720). In this way, the bending tool can securely grip the fillet members 200, such that the fillet 20 can be bent in various ways, for example, twisted (torqued) about the axis A. With a tool which engages in the openings 202 of the two outer fillet members 200, the fillet 20 can be shortened and/or compressed by pressing the two outer fillet members 200 toward each other, as a result of which the frame 201 of the central fillet member 200 bends, and the opening 202 of the central member 200 assumes a kind of rhombus shape, whose shorter diagonal is arranged along the axis A. In particular, only the two outer openings 202 are matched for positive engagement with the instrument of FIG. 11 and/or the shape 720. The central opening in each case is always smaller in order that it may not be inadvertently received by the shape 720 from FIG. 11. The central rhomboid member 200 always remains free as a result and there remains a generous distance between two pliers, see FIG. 11. The central member 200 prevents shearing of a fillet during rotation in the longitudinal axis and allows the material to "flow" in the movement.

The pliers shown in FIG. 12 is provided for the purpose of flattening the implant shoe 43 from FIG. 5 whose purpose is to create a connection to the fillet 44 from FIG. 7 and therefore said pliers has parallel closing recesses 811, 821 with edges 8110 or 8120 as per FIG. 12b.

A similar tool as per FIG. 12a has recesses 811, 821 with rear edges 8110, 8120 at an angle, said tool being positioned at the free corners of one of the quadratic frames 201 of the fillet members 200 for the purpose of lengthening a rhomboid-shaped fillet 200 in FIG. 3. The fillet 20 can be lengthened by pressing the free opposing corners of the frame 201 together. In this case, the opening 202 assumes a rhomboid shape, with the longer diagonal of the rhombus arranged along the axis A. This process can be performed on individual, multiple or all the members 200.

FIG. 4 shows a variant 3 of the implant 2 from FIG. 3. The implant 3 of this third embodiment differs from the implant 2 of the second embodiment only in that the implant components 3a and 3b, which are essentially the same as the implant component 1 described in connection with FIGS. 1 and 2, have in contrast to the second embodiment clamps 30a and 30b of different geometry. In the present case, the clamp 30a is larger than the clamp 30b, that is, it has a greater span w (w 3a>w3b). In this way, the implant 3 can be fixed at the sternum, with said first implant component 3a attached to a portion of the sternum of greater circumference, and the second implant component 3b attached to a portion of the sternum of smaller circumference. The length of the connecting fillet 30 can be adjusted to the spacing and geometry of the sternum by applying corresponding bending tools between the attaching portions of the implant components 3a and 3b. Similarly, the position of the implant components 3a and 3b can be set, e.g., the degree to which they are twisted toward one another about the axis A, and/or the angle between the planes spanned by the clamps 30a and 30b of the implant components 3a and/or 3b.

The implant or implant component 1 described in connection with FIGS. 1 and 2 can be referred to as a "single clip". The implants 2 and 3 described in FIGS. 3 and 4 thus consist of single clips 2a, 2b and/or 3a, 3b each connected by a fillet 20 and/or 30.

FIG. 5 shows a fourth embodiment of an inventive implant 4. The implant 4 consists essentially of an implant component 4a, which corresponds in structure to an implant component 1 as per the first embodiment. The implant component 4 is therefore not described in further detail.

In the fourth embodiment of the invention, a holder or an attaching device 42, which has a base 420 having a contact surface for a connecting member 44 (see FIG. 7) is contiguous with a protrusion 412 of the two protrusions 411, 412 of the member 41 for the purpose of providing engagement with and/or support for a bending tool. In addition, the holder 42 has side fillets on both sides of the base 420 that extend upward from the contact surface of the base 420, each of the fillets having an inwardly extending guide protrusion at its top end. The fillets and the guide protrusions each form an L-shaped guide member 43, which together form a guide for the purpose of guided insertion of a connecting member 44. By virtue of the L-shaped configuration, the guide members 43, together with the edge portions of the contact surface of the base 420, form, perpendicular to the axis A, a guide receptacle (on both sides) which has a U-shaped cross-section and into which the rod-shaped connecting member 44 can be inserted in the direction of the axis A.

In addition, the opposite edges of the guide protrusions extending from the fillets each have a toothed structure 430.

FIG. 6 shows a fifth embodiment of the implant as per the invention. This embodiment corresponds essentially to the embodiments shown in FIGS. 3 and 4, the difference being that, in addition to the first implant component 2a and/or 3a and the second implant component 2b and/or 3b, which are connected by connecting fillets 20 and/or 30, provision is made for a third implant component 2c/3c which is connected to the second implant component 2b/3b via a further connecting fillet 20'/30'. All three implant components 2a/3a, 2b/3b, 2c/3c have the same structure. The span of the clamps of the three implant components 2a/3a, 2b/3b, 2c/3c can be the same size or different.

FIG. 7 shows a connecting member 44 that can be inserted into the guide 43. The connecting member 44 has a rod-shaped body 440 having a recess 441 on both sides. These should be provided at least in the end portion or connecting portion. The recess 441 is defined by a horizontal and a vertical wall. The vertical wall has a toothed structure 442 that is complementary to the toothed structure 430 of the guide protrusions of the guide members 43. Whereas the horizontal walls extending outwardly on both sides can be inserted into the U-shaped receptacles of the guide members 43, the rod-shaped connecting member 44 can be aligned at the implant 4, and be locked by compressing the fillets of the guide 43, whereby the teeth 430 of the guide 43 and the teeth 442 of the connecting member 44 are brought into mutual engagement. However, across its entire length and preferably on both sides, the rod 44 has a recess 441 and a toothed structure 442, as shown in FIG. 7. In this way, it is possible to "thread" a plurality of implants 4, at least two implants 4, onto the rod. That is to say, the implants 4 are spaced apart in a line along the longitudinal axis of the rod 44. The distances between the line of implants 4 are based on the distances of the intercostal spaces in the axial sternum direction. It is possible to vary the length to match required distances arising from the given anatomy. The guides or shoe parts 43 of the outer implants are aligned counter to each other; however, to an extent depending on the space between the intercostal spaces, they may be aligned in series. Where one or more central implants 4 are provided, the guide 43 can point, relative to the member 41 for the purpose of providing engagement with, support for and/or positioning of a bending tool, in opposing directions, that is to say, toward opposite ends of the rod 44. Alignment of the implant 4 varies with the anatomic needs.

The other end portion and/or connecting portion of the rod-shaped connecting member 44 is usually connected to a further implant 4 as per the fourth embodiment from FIG. 5. In this construction, the position and distance to which the rod-shaped connecting member 44 is inserted into the guides 43 of the implant 4 can be varied, set and fixed on both sides. As a result, the length of the connection between two implants 4 can be set according to need. It is also conceivable for implants 4 to be arranged and attached at any point along the rod-shaped connecting member 44, e.g., roughly in the middle as well.

In the connecting portion between the protrusion 412 and the holding member 42, provision is made in the present embodiment for a constricted region, which can be formed so as to be bendable and/or twistable. The circular holes arranged on both sides of this portion are intended for the purpose of engaging a bending tool (e.g., three-point pliers). However, the connecting portion can also be omitted, that is to say, the guide 43 can be connected directly to the protrusion 412.

The implant described in connection with FIGS. 1 and 2 and/or the implant component 1 can be referred to as a "single clip". The implants 2 and 3 described in FIGS. 3 and 4 thus consist of single clips 2a, 2b and/or 3a, 3b, each connected by a fillet 20 and/or 30. The implant 4 described in FIG. 6 consists of a single clip 4a and a holder 42 attached thereto.

In an implant system consisting of several implants and possibly tools, single clips as per FIG. 1 can be provided in different sizes, e.g. with different clamp spans. Implants as per FIG. 3, 4, 5 or 6 can also be provided with single clips of different clamp size. In implant 2 as per the second embodiment, the single clips 2a and 2b are essentially identical, i.e. they have the same size. In the third embodiment as per FIG. 4, the two single clips 3a and 3b present in the implant 3 have been given a different span. In an implant system, implants 3 as per the third embodiment with clamps of different proportions and different absolute sizes can be present. For easier handling, the different sizes of the implants 1, 2, 3, 4 and 5 can be made identifiable, e.g., by their color, and thus made easier to distinguish from each other visually. The different colors form a color code.

FIG. 8 schematically illustrates which cross-section the clamps of the implants of the first, second, and third embodiment can have (right side). On the left side are drawn ovals which correspond to that optimum cross-sectional area of the sternum which provides the optimum fit for the single clip.

FIG. 9a shows a first bending tool 5 which can cooperate with all of the described implants 1, 2, 3, 4, 5 and 6. The bending tool is pliers-shaped and has two symmetrical jaws 51, 52. Between the jaws 51 and 52 is arranged a hold-down device 53. This is essentially connected to an articulated joint of the pliers and, upon actuation of the pliers, is guided such that it always maintains a central position between the jaws 51 and 52.

The hold-down device 53 (see FIG. 9b) has essentially one arm 530, at the lower end of which a platform 531 extends perpendicularly to the front. The platform 531 is rectangular or square. Extending downwardly from the platform 531 are four pins 532 which are arranged such that they engage in angles formed by the outer edges 1000 (see FIG. 2) of the connecting portion 100 of the implant 1 and the respective side edges 1011, 1012, 1021, 1022 of the protrusions 111 and/or 112. In this way, the platform 530 can be positioned securely at the member 11 for the purpose of providing engagement and/or positionally stable support. The platform 531 can at least be fixed or defined with respect to movement in its plane. The platform 531 and the pins 532 form a positioning member for the tool 5.

The jaws 51 and 52 each have grooves, that is to say, the lower ends of the jaws 51 and 52 each have a central recess which is bounded by downwardly projecting lateral guide fillets. In this way, the jaws 51 and 52 can be guided from above (that is, from the connecting portion 100) along the clamp members, e.g. the prongs 101 and/or 102, in the direction of the free ends of the prongs 101 and/or 102.

The first bending tool 5 is used as a clamp-positioning pliers. First, the grasping clamping member 100, 101, 102 is placed around the sternum. With the aid of the bending tool 5, the prongs 101 and 102 of the clamp 10 are bent inwardly towards each other. The clamp ends do not need to be molded/bent/shaped exactly to the back side of the sternum. The clamp ends are bent inward by about 45° with the aid of the tool 5.

As it is not possible to hold implants at the sternum by means of a clamp before fixing, and as it is known that the clamp 10 "lifts up" as it is being deformed, the invention provides for a hold-down device 53 which cooperates at the corresponding member 11 for the purpose of providing engagement with or support for the implant component 1 (similar considerations apply of course to 2a, 2b, 3a, 3b, 4a). It goes without saying that attaching of the clamp 10 to each of the previously described implants 1, 2, 3, 4.5 or 6 can be performed with the aid of the tool 5.

FIGS. 10a and 10b show a further bending tool 6 which is also formed like a pliers. However, the jaws 61 and 62 are formed asymmetrically. The longer jaw 61 has a curved structure, with the end 610 bent inwardly so as to grip a clamp. Moreover, the end 610 has a sliding surface which can slide along or be guided along the outside of the prongs 101, 102 (see FIG. 1) of the single clip used in the implants. In order to improve guiding, guide protrusions may be provided on both sides of the sliding surface.

The end portion of the shorter of the jaws 62 has two protruding pins/fillets 620 which are configured and positioned such that they can engage at one side of that member 11 for the purpose of providing engagement with or support for one of the single clips 1, while the longer jaw slides along the outside of one of the prongs 101 and/or 102 of the single clip 1 and downwardly in the direction of the free end of one of the prongs 101 and/or 102, and molds the end of the prong 101 and/or 102 onto the bone surface in the back region of the sternum. The longer of the jaws is guided in a circular arc in the direction of the clamp ends and molds the clamp ends, which the surgeons cannot see but can feel, onto the sternum.

The guide surface of the longer of the jaws 61 is preferably configured as a rounded surface. The recess between the fillets 620 of the inside of the shorter jaw 62 can be rounded or beveled in order that slipping of the clamp from the member 11 may be prevented. In other words, the inner edge of the surface between the fillets 620 is machined or beveled in order that the shorter jaw 620 may be securely held at the member 11 during downward movement of the longer jaw 610.

A third bending tool 7, which is also formed like pliers, is shown in FIG. 11. Its purpose is to cooperate with the second and third embodiments of the invention. Whereas a first jaw 71 of the tool 7 has an essentially smooth inner side, the second jaw 72 has a protrusion 720 that is formed so as to complement the openings 202 and/or 302 (see FIGS. 3, 4) of the fillets 20 and/or 30 of the implants 2 and/or 3. The protrusion 720 engages with one of the openings 202, 302. A corresponding protrusion 720 of a further pliers 7 can engage in another opening 202, 302 of the same implant 2 and/or 3. Then, one of the pliers 7 can be actuated, e.g., rotated with respect to the other pliers 7. The pliers 7 grip the fillet 20 and/or 30 so securely that this can be bent with the aid of the tools 7 in a defined manner, e.g., twisted (torqued) along the axis of A. Due to the non-circular shape of the openings 202 (roughly quadratic or rhomboid) in the fillets 20, 30, the fillet 20, 30 can also be bent in both directions in the plane which is spanned by the fillet, or the fillet 20, 30 can be bent upward and/or downward in the plane of symmetry extending along the axis A.

In an embodiment not shown, the jaw 72 on the inner side of the pliers-like tool 7, can be configured so as to be essentially flat/planar, with the protrusion 720 projecting from this planar surface, that is to say, the protrusion extends from the planar surface of the inner side of the jaw 72, such that the surface of the protrusion 720 is not flush with the inner side of the jaw 72. Laterally, in this embodiment, which is not shown, the I-shaped jaw 72 terminates roughly at the respective corner of the protrusion 720.

FIGS. 12a and 12b show a fourth bending tool 8 in the form of a pliers with two jaws 81 and 82. The jaws 81 and 82 each have a front side which terminates at an inner edge 810 and/or 820. In the region of the inner edges 810 and 820 is formed a recess 811 and/or 821, which, proceeding from the edge, extends outwardly and has an outer contour 8110 and/or 8210 which can be curved or outwardly bulged. FIG. 12c shows the bending tool from the front, with the outer contours 8110 and 8120 of the recesses 811 or 821 configured so as to be concave, and in particular in such a way that they can accommodate rhomboid frame sections 201 by positive locking. The recesses 811 and 821 can be formed so as to have a contour that matches the rhomboid of the implant fillet. The curvature and/or bulge is adjusted such that the recesses 811 and 821 together can receive a fillet member 200, 300. Upon actuation of the tool 8, the rear walls 8110 and 8120 of the recesses 811 and/or 821 grip the frame 201 of the fillet member 200, 300. The opposing fillet halves can be deformed by further actuations, such that the opening 202, 302 is deformed into a rhomboid shape whose longer diagonal lies on the axis A. In this way, the fillet 20 and/or 30 is extended. The tool from FIGS. 12a and 12b is required for the purpose of connecting implant components as per FIG. 5 and FIG. 6; for the purpose of extending the fillet in the pliers described as per FIG. 12c, one jaw end is provided with a rhomboid guide.

Further bending tools can conceivably be used, which at the implant either can be positioned and fixed in a defined manner at the members 11 for the purpose of providing engagement with and/or grip for and/or support for a single clip 1, 2a, 2b, 3a, 3b, 4a, 5a by gripping frame sections 201, 301 of the frame 201 of the fillet members 200, 300 and/or by engaging with that opening 202, 302 of a fillet 200, 300 which is defined by the frame 201, 301, or can grip the implant 1, 2, 3, 4, 5, especially by positive locking, such that bending movements can be transmitted to individual components or parts of the implant 1, 2, 3, 4, 5. Thus, manipulation and deformation of the implant can be performed with the greatest possible reliability and in the shortest possible time.

Thus, a bending tool is conceivable, for example, which can compress a fillet 20, 30 in the second and third embodiments 2 and 3 of the invention. To this end, a protrusion can be formed on each of both jaws of a pliers-like instrument, said protrusion corresponding to the contour of the openings 202, 302 of the fillet members 200, 300. These protrusions can engage with openings 202, 203 of the outer fillet members 200, 300. Upon actuation of the pliers, the jaws are guided toward one another, as a result of which compression of the central fillet member 200, 300 occurs, such that the opening 202, 302 of the central fillet member 200, 300 is deformed into a rhomboid whose longer diagonal is perpendicular to the axis A. In this way, the fillet 20, 30 is shortened overall.

Figure 13:
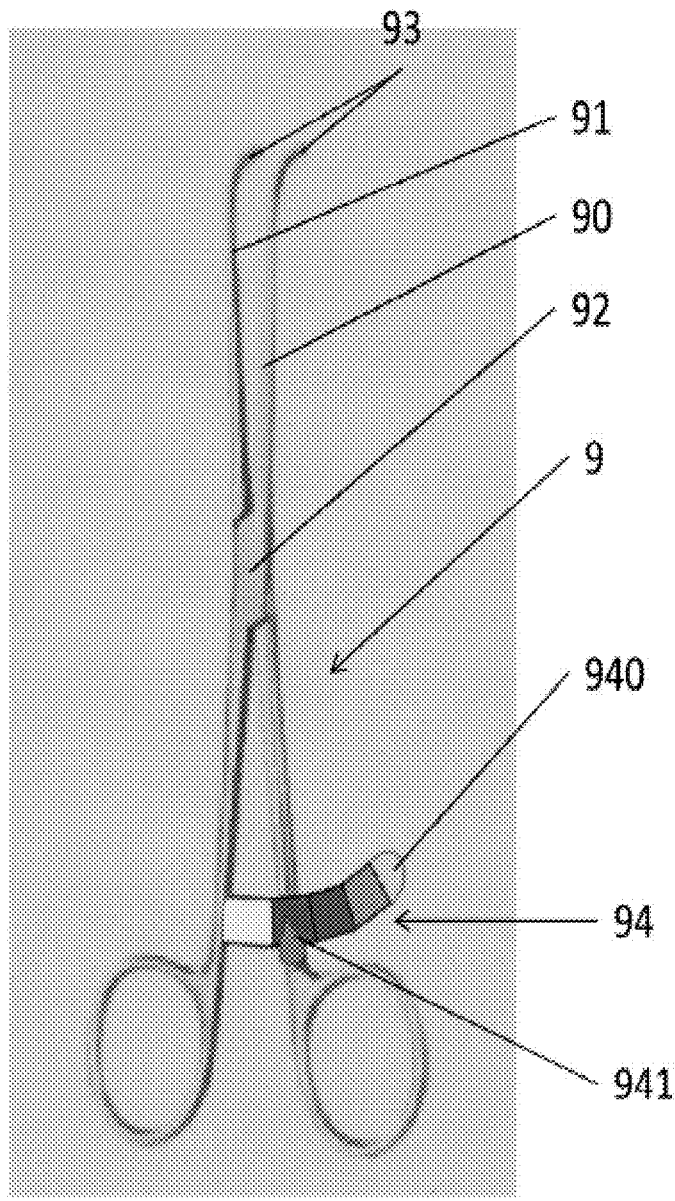

FIG. 13 shows an inventive implant-selection tool 9. This has two levers 90, 91 that move towards each other and are mounted rotatably with respect to one another about an axis 92.

The instrument 9 is intended to perform two different tasks: Firstly, the instrument 9 is intended to bluntly dissect near-sternum perforations of the soft tissue to accommodate the clamp ends. Blunt dissection is important for preventing damage to blood vessels. The jaw 93 is bent downward such that, irrespective of the penetration depth of the angled jaw parts, a specific "reading" is transmitted to the scale 94. The jaw ends descend parallel to the outsides of the sternum and thus transmit the sternum width to the scale 940. This ensures that perpendicular, parallel penetration into the soft tissues to the left and right of the sternum can be carried out, which is why the instrument must in any event be bent and does not have to be straight. This process is intended to create holes that can readily accommodate the implant ends, by no means not just pin-prick perforations.

The second task of the instrument is to determine via a scale 940 that implant which matches the width of the clamps. The measuring device 94 has a color-graduated scale 940, which is a thin, curved metal strip, which similarly on the other side has the same colors that define the implant type sizes. The scale is attached to one of the two levers 91. This means that, when the indicator 941 (which is attached to the other lever 90) points to a particular field on the scale 940 during measurement of the distance between the jaw ends 93, an implant whose size corresponds to this field is to be used. The measuring device 94 is configured as a kind of measuring compass.

When the scale 940 with the different colored fields is being prepared, care must be taken to ensure that it is resistant to wear and that the colors do not change, as the instrument has to be used for every procedure and is also exposed to high levels of wear in terms of cleaning and sterilization processes. The scale 940 should therefore be made from a resilient material. A suitable material would be titanium, since this material can be anodized. Also conceivable is a scale made from different resilient, resistant materials that can be permanently color coded, e.g., a scale with corresponding wear-resistant colors. In any case, the scale is aligned in a similar manner to different types and sizes of implants.

In order to perform the measurement as precisely as possible, the jaw parts 93 must be of a relatively rigid construction, so that that the readings on the scale may not be impaired by excessive flexibility. In addition, the soft tissues can be perforated with a certain amount of pressure if the jaw parts are sufficiently rigid.

The correct implant size is determined by gripping that rib section to which the implant is to be applied with the ends of the levers, that is, with the two halves of the jaw part 93, and then reading the correct size of the implant on the scale 940.

The invention claimed is:

1. An implant component (1, 2*a*, 2*b*, 3*a*, 3*b*, 4*a*) for sternal osteosynthesis, comprising:
    a clamp (10, 20, 30, 40) having a first prong (101) and a second prong (102),
    wherein the first prong (101) and the second prong (102) are connected by a connecting portion (100),
    wherein the first and second prongs are bendable to be bent inward under the sternum by use of a bending tool, and
    wherein a member is located at the connecting portion (100), the member (11) providing mutual engagement with a compatible hold-down device of a positioning member of the bending tool (5, 6) in order to prevent lifting-up of the clamp during a bending operation,
    wherein the member (11) that provides engagement comprises a first protrusion (111), which extends laterally from a first side of the connecting portion (100), and a second protrusion (112), which extends laterally from the opposite side of the connecting portion (100), and
    wherein the first protrusion (111) and/or the second protrusion (112) have a first end edge (1110) and/or a second end edge (1120) and two side edges (1111, 1112, 1121, 1122), with the side edges (1111, 1112, 1121, 1122) of the protrusion (111, 112) and/or of the protrusions (111, 112) forming an angle with the respective side edge (1000) of the connecting portion (100) that provides engagement with the positioning member of the bending tool and that makes contact with the respective edges.

2. The implant component (1, 2*a*, 2*b*, 3*a*, 3*b*, 4*a*) in accordance with claim 1, wherein
    at least one of the first end edge (1110) and the second end edge (1120) is curved.

3. The implant component (1, 2*a*, 2*b*, 3*a*, 3*b*, 4*a*) in accordance with claim 1, wherein
    the surface of the member (11) that provides engagement is flush with the connecting portion (100) of the clamp (10).

4. The implant component (1, 2*a*, 2*b*, 3*a*, 3*b*, 4*a*) in accordance with claim 1, wherein
    at least one of the first protrusion (111) and the second protrusion (112) has the same thickness (100) as the connecting portion of the implant (1).

5. An implant (2, 3) for sternal osteosynthesis, comprising:
    a first implant component (2*a*, 3*a*) comprising a clamp (10, 20, 30, 40) having a first prong (101) and a second prong (102),
    wherein the first prong (101) and the second prong (102) of the first implant component are connected by a connecting portion (100),
    wherein the first and second prongs of the first implant component are bendable to be bent inward under the sternum by means of a bending tool,
    wherein a first member (11) is located at the connecting portion (100) of the first implant component, the first member (11) providing mutual engagement with a hold-down device of a compatible positioning member of the bending tool (5, 6) in order to prevent lifting-up of the clamp during a bending operation;
    a second implant component (2*b*, 3*b*) comprising a clamp (10, 20, 30, 40) having a first prong (101) and a second prong (102),
    wherein the first and second prongs of the second implant component are bendable to be bent inward under the sternum by means of the bending tool, and
    wherein the first prong (101) and the second prong (102) of the second implant component are connected by a connecting portion (100),
    wherein a second member (11) is located at the connecting portion (100) of the second implant, the second member (11) providing mutual engagement with a compatible hold-down device of a positioning member of the bending tool (5, 6) in order to prevent lifting-up of the clamp during the bending operation; and
    a connecting fillet (20, 30), which connects the first implant component (2*a*, 3*a*) and the second implant component (2*b*, 3*b*).

6. The implant (2, 3) in accordance with claim 5, wherein
    wherein the connecting fillet (20, 30) has at least one fillet member (200, 300) arranged adjacently along an axis (A), with the fillet member (200, 300) having a frame (201, 301) that defines an opening (202, 302), and
    the frame (201, 301) of the fillet member(s) (200, 300) defines a roughly rectangular opening (202, 302), with the frame (201, 301) so arranged that a diagonal of the rectangular opening (202, 302) along the central axis (A), which extends perpendicularly to the clamps (2*a*, 2*b*, 3*a*, 3*b*) along the connecting fillet (20, 30), lies on the axis (A).

7. The implant (2, 3) in accordance with claim 5, wherein
    the connecting fillet (20, 30) has two outer fillet members (200, 300) and one or more internal fillet members (200, 300) arranged adjacently in series, with the two outer fillet members (200, 300) each arranged at one end edge of the protrusion (211*a*, 212*b*) of the first implant component (2*a*, 3*a*) and/or of the second implant component (2*b*, 3*b*).

8. The implant (2, 3) in accordance with claim 5, wherein the connecting fillet (20, 30) has the same thickness as the first member (11) that provides engagement.

9. The implant (3) in accordance with claim 5, wherein the clamp of the first implant component (3a) has a different span than the clamp of the second implant component (3b).

10. The implant (2, 3) in accordance with claim 5, wherein the connecting fillet (20, 30) has at least one fillet member (200, 300) arranged adjacently along an axis (A), with the fillet member (200, 300) having a frame (201, 301) that defines an opening (202, 302).

11. The implant (2, 3) in accordance with claim 5, wherein the connecting fillet (20, 30) has plural fillet members (200, 300) arranged adjacently along an axis (A), with the fillet members (200, 300) each having a frame (201, 301) that defines an opening (202, 302).

12. The implant (2, 3) in accordance with claim 11, wherein
the frames (201, 301) of the fillet member(s) (200, 300) define a roughly rectangular opening (202, 302), with the frames (201, 301) so arranged that a diagonal of the rectangular opening (202, 302) along the central axis (A), which extends perpendicularly to the clamps (2a, 2b, 3a, 3b) along the connecting fillet (20, 30), lies on the axis (A).

13. The implant (2, 3) in accordance with claim 5, wherein the connecting fillet (20, 30) has the same thickness as the clamp.

14. The implant (2, 3) in accordance with claim 5, wherein the connecting fillet (20, 30) has the same thickness as the clamp and the first member (11) that provides engagement.

15. The implant in accordance with claim 5,
wherein the first member (11) comprises a first protrusion (111), which extends laterally from a first side of the connecting portion (100), and a second protrusion (112), which extends laterally from the opposite side of the connecting portion (100), and
wherein the first protrusion (111) and the second protrusion (112) have a first end edge (1110) and a second end edge (1120) and two side edges (1111, 1112, 1121, 1122), with the side edges (1111, 1112, 1121, 1122) of the protrusion (111, 112) and of the protrusions (111, 112) forming an angle with the respective side edge (1000) of the connecting portion (100) that provides engagement with the positioning member of the bending tool and that makes contact with the respective edges.

16. The implant in accordance with claim 5,
wherein the first member (11) comprises a first protrusion (111), which extends laterally from a first side of the connecting portion (100), and a second protrusion (112), which extends laterally from the opposite side of the connecting portion (100), and
wherein at least one of the first and second protrusions have a at least one end edge and two side edges, with the side edges of the at least one protrusion (111, 112) forming an angle with the respective side edge (1000) of the connecting portion (100) that provides engagement with the positioning member of the bending tool and that makes contact with the respective edges.

* * * * *